United States Patent [19]

Möller et al.

[11] 4,425,327
[45] Jan. 10, 1984

[54] METHOD OF SUPPRESSING BODY ODOR WITH AMINOBENZOIC ACID AMIDES

[75] Inventors: Hinrich Möller; Rainer Osberghaus, both of Düsseldorf, Fed. Rep. of Germany

[73] Assignee: Henkel Kommanditgesellschaft auf Aktien, Düsseldorf-Holthausen, Fed. Rep. of Germany

[21] Appl. No.: 236,816

[22] Filed: Feb. 23, 1981

[30] Foreign Application Priority Data

Mar. 13, 1980 [DE] Fed. Rep. of Germany ....... 3009542

[51] Int. Cl.³ .................. A61K 7/32; A61K 7/035
[52] U.S. Cl. .................. 424/65; 424/DIG. 5; 424/47; 424/69
[58] Field of Search ............ 424/65, 69, DIG. 5

[56] References Cited

U.S. PATENT DOCUMENTS

| | | | |
|---|---|---|---|
| 2,230,082 | 1/1941 | Montenier | 424/68 |
| 2,294,140 | 8/1942 | Taylor | 424/65 X |
| 2,617,824 | 11/1952 | Moore et al. | 424/324 X |
| 2,762,822 | 9/1956 | Vagenius | 424/65 |
| 4,010,252 | 3/1977 | Hewitt | 424/68 |

FOREIGN PATENT DOCUMENTS

| | | | |
|---|---|---|---|
| 867135 | 2/1953 | Fed. Rep. of Germany | 424/60 |
| 1295710 | 5/1962 | France | 424/60 |
| 1568910 | 4/1969 | France | 424/230 |
| 46-29847 | 8/1971 | Japan | 424/324 |
| 342700 | 1/1960 | Switzerland | 424/60 |
| 653027 | 5/1951 | United Kingdom | 424/320 |

OTHER PUBLICATIONS

Okeida, Chem. Abs., 1956, vol. 50, p. 14865.

Primary Examiner—Dale R. Ore
Attorney, Agent, or Firm—Hammond & Littell, Weissenberger and Muserlian

[57] ABSTRACT

This invention is directed to a cosmetic deodorant composition comprising:

(a) from about 0.1 to 5 percent by weight, based on the weight of the total composition, of aminobenzoic acid amides of the formula

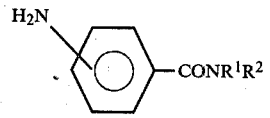

wherein $R^1$ and $R^2$, which may be the same or different, each represent hydrogen, an alkyl of from 1 to 12 carbon atoms; a hydroxyalkyl of from 2 to 4 carbon atoms; an aryl; an aralkyl or carboxyalkyl with from 1 to 3 carbon atoms in the alkyl moiety; or an alkoxyalkyl with from 1 to 8 carbon atoms in the alkoxy moiety and from 1 to 3 carbon atoms in the alkyl moiety, or $R^1$ and $R^2$ together with the amide nitrogen form an optionally substituted heterocyclic ring; and (b) the remainder conventional cosmetic deodorant composition compounds.

5 Claims, No Drawings

METHOD OF SUPPRESSING BODY ODOR WITH AMINOBENZOIC ACID AMIDES

FIELD OF THE INVENTION

This invention is directed to cosmetic deodorant compositions. More specifically, this invention is directed to cosmetic deodorant compositions containing aminobenzoic acid amides.

BACKGROUND OF THE INVENTION

It is known that the offensive odor accompanying human perspiration is caused by the bacterial decomposition of the initially odorless perspiration. Consequently, there have been numerous proposals to correct this problem, but to date there has not been a universally satisfactory solution. There are basically two approaches that have been taken for the solution of the problem: first, the use of antimicrobial compounds for the killing of bacterial skin flora or the inhibition of its growth, which causes the decomposition of the perspiration, and second, the use of compounds that prevent the formation of perspiration. Besides these, agents with a purely absorptive action and those that cover up odor play a completely subordinate role.

The concurrent use of antiperspirants which prevent the formation of perspiration as well as of antimicrobial compounds is a problem since, in the former case, an intervention in the physiological process of the formation of perspiration takes place, which is undesirable and, in the latter, an action on the natural skin flora accompanies the inhibition of the growth of the bacteria causing the decomposition of perspiration. In addition, the prolonged use of antiperspirants can result in skin irritation and changes of the skin.

The cosmetic agents with deodorant action are all substances with a content of antimicrobial compounds, such as, for example, phenol derivatives with or without halide substituents, quaternary ammonium compounds, and derivatives of amino acids with a disinfectant effect. Although the use of deodorants does not provoke the danger of skin irritation to the great extent caused by the application of antiperspirants, occasional intolerance, photosensitization, and toxic side effects of varying degree have been observed, in addition to damage of the normal skin flora, with the regular use of deodorants containing antimicrobial agents. Furthermore, most of these products are not odorless, and some have a slightly phenolic odor that results in their rejection by many consumers. Consequently, there has been a continuing effort to produce cosmetic agents for the suppression of body odor with a very good deodorant action and relatively complete freedom from side effects.

OBJECTS OF THE INVENTION

It is an object of the invention to provide novel cosmetic deodorant compositions.

It is another object of the invention to provide a cosmetic deodorant composition having very good deodorant action and relatively complete freedom from side effects.

It is a further object of the invention to provide cosmetic deodorant compositions containing aminobenzoic acid amides of the formula

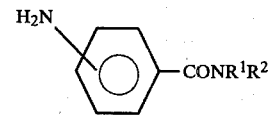

wherein $R^1$ and $R^2$, which may be the same or different, each represent hydrogen; an alkyl of from 1 to 12 carbon atoms; a hydroxyalkyl of from 2 to 4 carbon atoms; an aryl; an aralkyl or carboxyalkyl with from 1 to 3 carbon atoms in the alkyl moiety; or an alkoxyalkyl with from 1 to 8 carbon atoms in the alkoxy moiety and from 1 to 3 carbon atoms in the alkyl moiety, or R and $R^2$ together with the amide nitrogen form an optionally substituted heterocyclic ring.

These and other objects of the invention will become more apparent in the discussion below.

DETAILED DESCRIPTION OF THE INVENTION

Applicants have discovered cosmetic deodorant compositions that have very good deodorant properties and that are relatively free from side effects. The cosmetic deodorant compositions contain aminobenzoic acid amides of the formula

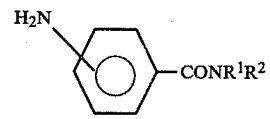

wherein $R^1$ and $R^2$, which may be the same or different, each represent hydrogen; an alkyl of from 1 to 12 carbon atoms; a hydroxyalkyl of from 2 to 4 carbon atoms; an aryl; an aralkyl or carboxyalkyl with from 1 to 3 carbon atoms in the alkyl moiety; or an alkoxyalkyl with from 1 to 8 carbon atoms in the alkoxy moiety and from 1 to 3 carbon atoms in the alkyl moiety, or $R^1$ and $R^2$ together with the amide nitrogen form an optionally substituted heterocyclic ring. In a preferred form of the invention, $R^1$ and $R^2$ may each represent an alkyl of from 1 to 12 carbon atoms; a hydroxyalkyl of from 2 to 4 carbon atoms; a phenyl or benzyl radical; a carboxyalkyl with from 1 to 3 carbon atoms in the alkyl moiety; or an alkoxyalkyl with from 1 to 8 carbon atoms in the alkoxy moiety and from 1 to 3 carbon atoms in the alkyl moiety, or $R^1$ and $R^2$ together with the amide nitrogen form a piperidino or morpholino group which may be optionally substituted by one or more lower alkyl or halide groups.

The aminobenzoic acid amides to be used according to the invention are prepared by generally known methods of organic synthesis. Thus the nitrobenzamides are prepared first by aminolysis of the nitrobenzoyl chlorides, and the respective aminobenzoic acid amides are prepared from these by catalytic hydrogenation.

Carboxylic acids on which the aminobenzoic acid amides to be used according to the invention are based include, for example, meta- and para-aminobenzoic acid.

Suitable amide components, in addition to a primary amide, include, for example, methyl-, dimethyl-, ethyl-, diethyl-, propyl-, dipropyl-, methylpropyl-, di-2-propyl-, butyl-, dibutyl-, sec.butyl-, tert.butyl-, hexyl-, dihexyl-, 2-ethylhexyl-, octyl-, decyl, dodecyl, 2-hydroxyethyl-, di-(3-hydroxypropyl)-, 3-methoxypropyl-, 3-(2-ethylhexoxy)propyl-, and benzylamide; anilide; N-methylanilide; piperidide; 2-methyl-, 3-methyl-, 4-methyl-, 2,4-dimethyl-, and 3,5-dimethylpiperidide; morpholide; and 2,6-dimethylmorpholide.

Aminobenzoic acid amides to be used according to the invention include, for example, p-aminobenzoic acid diethylamide, p-aminobenzoic acid dipropylamide, p-aminobenzoic acid anilide, p-aminobenzoic acid piperidide, p-aminobenzoic acid 4-methylpiperidide, p-aminobenzoic acid 3-methylpiperidide, and p-aminobenzoic acid carboxymethylamide.

For the preparation of the cosmetic deodorant compositions according to the invention, the aminobenzoic acid amides may be incorporated in all products normally used for deodorants, such as powders, sticks, roll-ons, and sprays, the deodorant spray being the preferred product for application. The incorporation is achieved in a known manner by simple mixing or dissolution in other components of the product such as solvents, waxes, fat substances, polyglycols, or powder bases. The cosmetic deodorant compositions contain the aminobenzoic acid amides in amounts of from about 0.1 to 5 percent by weight, preferably from about 0.5 to 2 percent by weight, based on the weight of the total composition.

The cosmetic deodorant compositions according to the invention preferably contain the aminobenzoic acid amides as the sole deodorant active substances; however, a combination with other deodorant active substances is possible as well.

The deodorizing effect of the cosmetic compositions can be increased when these contain one or more antioxidants in addition to the aminobenzoic acid amides in amounts of from about 0.01 to 1 percent by weight, preferably from about 0.05 to 0.5 percent by weight, based on the weight of the total product. Antioxidants useful in the compositions according to the invention include all antioxidants normally used in the pharmaceutical, cosmetic, and food sectors, including, for example, the following: butylhydroxytoluene, butylhydroxyanisol, guaiac resin, lecithin, nordihydroguaiaretic acid, propyl gallate, octyl gallate, dodecyl gallate, tocopherols, trihydroxybutyrophenone, ascorbic acid, ascorbyl palmitate, dilaurylthiodipropionate, distearylthiodipropionate, monoisopropyl citrate, thiodipropionic acid, and citraconic acid.

The following examples are intended to illustrate the invention and are not to be construed as limiting the invention thereto.

EXAMPLES

Some of the aminobenzoic acid amides to be used according to the invention, and the preparation thereof, are described in greater detail below.

EXAMPLE 1 p-Aminobenzoic Acid Dipropylamide (a) p-Nitrobenzoic acid dipropylamide

An amount of 37.1 gm (0.2 mol) of p-nitrobenzoyl chloride in 300 ml of ether were added dropwise, with agitation and at room temperature, into a solution of 50.6 gm (0.5 mol) of dipropylamine in 400 ml of ether. Then, the mixture was agitated for one hour at room temperature and one hour at boiling temperature, the reaction mixture was treated with dilute hydrochloric acid, and the ether phase washed with water and evaporated. An amount of 44.3 gm of p-nitrobenzoic acid dipropylamide in the form of a light-yellow, oily residue was obtained.

(b) p-Aminobenzoic acid dipropylamide

An amount of 44.3 gm (0.2 mol) of the p-nitrobenzoic acid dipropylamide from step (a) was dissolved in 500 ml of ethanol and, after addition of 5 gm of palladium active charcoal (5%), hydrogenated at 50° C. and 60 bar pressure. After filtration, evaporation of the ethanol solution, and recrystallization of the residue (34.1 gm) from ether, 26.7 gm of p-aminobenzoic acid dipropylamide with a melting point of 78°-79° C. were obtained.

By use of procedures analogous to those described above, the following compounds were prepared:

(a) p-Aminobenzoic acid anilide, m.p. 130° C.

(b) p-Aminobenzoic acid diethylamide, m.p. 122°-123° C.

(c) p-Aminobenzoic acid piperidide, m.p. 160°-161° C.

(d) p-Aminobenzoic acid 4-methylpiperidide, m.p. 114°-115° C.

(e) p-Aminobenzoic acid 3-methylpiperidide, m.p. 155° C.

(f) p-Aminobenzoic acid carboxymethylamide, m.p. 199°-200° C.

Several examples of cosmetic deodorant compositions according to the invention are given below.

EXAMPLE 2

Deodorant Stick

| Component | Amount (parts by weight) |
| --- | --- |
| 2-Octyldodecanol | 27.0 |
| Cetyl/stearyl alcohol | 4.0 |
| Sodium stearate | 9.0 |
| Coconut oil fatty acid monoethanolamide | 3.0 |
| Liquid paraffin | 4.0 |
| Propylene glycol | 2.0 |
| Ethanol | 49.0 |
| p-Aminobenzoic acid dipropylamide | 2.0 |
| | 100.0 |

EXAMPLE 3

Deodorant Powder

| Component | Amount (parts by weight) |
| --- | --- |
| Rice starch | 27.0 |
| Magnesium carbonate | 3.0 |
| Zinc oxide | 2.0 |
| Talc, extra fine | 81.0 |
| p-Aminobenzoic acid anilide | 2.0 |
| | 115.0 |

EXAMPLE 4

Deodorant Spray

| Component | Amount (parts by weight) |
| --- | --- |
| p-Aminobenzoic acid piperidide | 1.5 |
| Ethanol | 11.0 |
| Isopropanol | 20.5 |
| Isopropyl myristate | 2.0 |
| Propellant gas (Frigen 12/114 in a ratio of 60:40) | 65.0 |

-continued

| Component | Amount (parts by weight) |
|---|---|
| | 100.0 |

EXAMPLE 5

Deodorant Spray

| Component | Amount (parts by weight) |
|---|---|
| p-Aminobenzoic acid 4-methylpiperidide | 1.3 |
| Butylhydroxytoluene | 0.2 |
| Propylene glycol | 2.5 |
| Isopropyl myristate | 2.0 |
| Ethanol | 14.0 |
| Propellant gas (Frigen 11/12 in a ratio of 50:50) | 80.0 |
| | 100.0 |

EXAMPLE 6

Deodorant Cream

| Component | Amount (parts by weight) |
|---|---|
| Mixture of mono- and diglycerides of palmitic and stearic acid (Cutina MD ® from Dehydag) | 20.5 |
| Cetyl/stearyl alcohol + approximately 12 mols ethylene oxide (Eumulgin B1 ® from Dehydag) | 2.0 |
| p-Aminobenzoic acid carboxymethylamide | 1.3 |
| Butylhydroxytoluene | 0.2 |
| Water | 61.9 |
| p-Hydroxybenzoic acid methyl ester | 0.1 |
| Perfume oil | 1.0 |
| | 90.0 |

EXAMPLE 7

Deodorant for Pump Atomizer

| Component | Amount (parts by weight) |
|---|---|
| Ethanol | 85.0 |
| Isopropanol | 7.2 |
| p-Aminobenzoic acid 3-methylpiperidide | 1.5 |
| Butylhydroxytoluene | 0.3 |
| Perfume | 1.0 |
| Water | 5.0 |
| | 100.0 |

The following deodorant sprays were prepared for a comparison of the effectiveness.

EXAMPLE 8

| Component | Amount (parts by weight) |
|---|---|
| p-Aminobenzoic acid diethylamide | 1.5 |
| Isopropanol | 5.5 |
| Ethanol | 33.0 |
| Propellant gas (Frigen 12/114 in a ratio of 60:40) | 60.0 |
| | 100.0 |

COMPARISON EXAMPLE 8

| Component | Amount (parts by weight) |
|---|---|
| Caprylic/capric acid triglyceride | 1.5 |
| Isopropanol | 5.5 |
| Ethanol | 33.0 |
| Propellant gas (Frigen 12/114 in a ratio of 60:40) | 60.0 |
| | 100.0 |

Testing

A test group consisting of 15 female and 15 male participants first used for five days a soap ("Soap F") that did not contain an antimicrobial agents or any deodorants or antiperspirants. After this time, each participant received a T-shirt and instructions to treat one armpit with the deodorant spray of Example 8 ("Deodorant Spray A") on the morning of the sixth day, after washing with Soap F, and to leave the other armpit untreated for comparison, with one-half of the group treating the left armpit and the other half the right armpit. The development of odor was evaluated by the participants themselves as well as by two experienced cosmeticians, by sniffing of the T-shirts after 8 hours and 24 hours. Thereafter, the participants used only Soap F for one week. Subsequently, the test was repeated, treating the previously untreated armpit with Deodorant Spray A and using the other armpit for comparison.

All persons taking part in both tests determined a very good odor prevention with the Deodorant Spray A.

The test was repeated with the same test group in a completely analogous way, except that the deodorant spray of Comparison Example 8 ("Deodorant Spray B") was used instead of Deodorant Spray A. In this test, no significant reduction of odor could be observed with respect to use of Deodorant Spray B by any of the participants or the cosmeticians.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for suppressing body odor in a warm-blooded animal comprising applying topically to said warm-blooded animal an effective deodorant amount of a cosmetic deodorant composition which comprises:

(a) from about 0.1 to 5 percent by weight, based on the weight of the total composition, of aminobenzoic acid amides of the formula

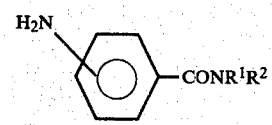

wherein $R^1$ and $R^2$, which may be the same or different, each represent an alkyl of from 1 to 12 carbon atoms; a hydroxyalkyl of from 2 to 4 carbon atoms; a phenyl or benzyl radical; a carboxyalkyl with from 1 to 3 carbon atoms in the alkyl moiety;

or an alkoxyalkyl with from 1 to 8 carbon atoms in the alkoxy moiety and from 1 to 3 carbon atoms in the alkyl moiety, or $R^1$ and $R^2$ together with the amide nitrogen form a piperidino or morpholino group which is unsubstituted or substituted by one or more methyl groups; and (b) the remainder inert cosmetic adjuvant compounds.

2. The process of claim 1, wherein the cosmetic deodorant composition comprises from about 0.5 to 2 percent by weight of component (a).

3. The process of claim 1, wherein the cosmetic deodorant composition also contains from about 0.01 to 1 percent by weight, based on the weight of the total composition, of antioxidants.

4. The process of claim 3, wherein the cosmetic deodorant composition contains from about 0.05 to 0.5 percent by weight, based on the weight of the total composition, of antioxidants.

5. The process of claim 3, wherein the antioxidants are selected from the group consisting of butylhydroxytoluene, butylhydroxyanisol, guaiac resin, lecithin, nordihydroguiaretic acid, propyl gallate, octyl gallate, dodecyl gallate, tocopherols, trihydroxybutyrophenone, ascorbic acid, ascorbyl palmitate, dilaurylthiodipropionate, distearylthiodipropionate, monoisopropyl citrate, thiodipropionic acid, and citraconic acid.

* * * * *